US012797002B2

(12) United States Patent
Marinos et al.

(10) Patent No.: US 12,797,002 B2
(45) Date of Patent: Nov. 17, 2026

(54) DEVICE AND METHOD FOR PENILE TUMESCENCE MONITORING

(71) Applicant: Adam Sensor Limited, London (GB)

(72) Inventors: Alexandrou Marinos, London (GB); Vasilakos Konstantinidis Christos, London (GB); Alexandrou Stefanos, London (GB); Solakis Vasileios, Athens (GR)

(73) Assignee: ADAM SENSOR LIMITED, London (GB)

( * ) Notice: Subject to any disclaimer, the term of this patent is extended or adjusted under 35 U.S.C. 154(b) by 144 days.

(21) Appl. No.: 18/763,865

(22) Filed: Jul. 3, 2024

(65) Prior Publication Data

US 2025/0040869 A1 Feb. 6, 2025

(30) Foreign Application Priority Data

Jul. 13, 2023 (EP) .................................... 23185197

(51) Int. Cl.
*A61B 5/00* (2006.01)
*A61B 5/107* (2006.01)

(52) U.S. Cl.
CPC ............ *A61B 5/4393* (2013.01); *A61B 5/107* (2013.01); *A61B 5/6813* (2013.01)

(58) Field of Classification Search
CPC ..... A61B 5/107; A61B 5/1072; A61B 5/1073; A61B 5/1075; A61B 5/4393; A61B 5/6813
See application file for complete search history.

(56) References Cited

U.S. PATENT DOCUMENTS 4,428,385 A * 1/1984 Morales ............... A61B 5/4393 600/587
4,747,415 A * 5/1988 Lavoisier ............. A61B 5/4393 600/587
(Continued)

FOREIGN PATENT DOCUMENTS

CN 109123893 A * 1/2019 ............... A43B 7/00
FR 2623995 A1 * 6/1989 ........... A61B 5/4393
(Continued)

OTHER PUBLICATIONS

CN109123893A—Machine Translation (Year: 2019).*
FR 2623995 with English Machine Translation (Year: 1989).*
KR 101592154 with English Machine Translation (Year: 2016).*

*Primary Examiner* — Adam J Eiseman
(74) *Attorney, Agent, or Firm* — The Watson IP Group; Jovan N. Jovanovic

(57) ABSTRACT

The present application discloses a device (10), a system, and a method for monitoring the penile tumescence. The device comprises a loop (3) positioned around the base of the penis. The loop (3) consists of two string threads mutually attached on both ends. Said string threads are wound up on a reel (1) having the centrally positioned spring (la). The movement of the reel (1) and the rotation of the magnet (2) indicate the penis diameter and the intensity of the erection. The magnetic rotary encoder (5) outputs the digital form of acquired data to a microprocessor (6). The data are preferably forwarded over a BLE communication module (7) to the mobile app, installed on a smart device that communicates with a remote computer.

13 Claims, 6 Drawing Sheets

(56) References Cited

U.S. PATENT DOCUMENTS

| | | | | | |
|---|---|---|---|---|---|
| 4,911,176 | A * | 3/1990 | Timm | A61B 5/4393 600/587 |
| 8,146,261 | B1 * | 4/2012 | Perry | G01B 3/1084 33/511 |
| 2010/0286547 | A1 * | 11/2010 | Aoude | A61B 5/1135 600/534 |
| 2014/0171767 | A1 * | 6/2014 | Hotaling | A61B 5/4393 600/323 |
| 2022/0087575 | A1 * | 3/2022 | Persidsky | G06F 3/0482 |

FOREIGN PATENT DOCUMENTS

| | | | | |
|---|---|---|---|---|
| KR | 101592154 | B1 * | 2/2016 | A61B 5/4393 |
| WO | WO-2007095906 | A2 * | 8/2007 | A61B 5/107 |
| WO | WO-2018231858 | A1 * | 12/2018 | A61B 5/7203 |

* cited by examiner

DEVICE AND METHOD FOR PENILE TUMESCENCE MONITORING

FIELD OF THE INVENTION

The present disclosure relates, in general, to the field of penile tumescence monitoring. Additionally, the present invention relates to providing a record of the penile rigidity and time intervals of the rigidity during a tumescence event. More particularly, the disclosure relates to a portable and wearable device for obtaining nocturnal penile tumescence data, a system comprising said device and a method for use thereof.

BACKGROUND OF THE INVENTION

Monitoring of penile tumescence is known in the art. The device such as RigiScan Plus Monitor is an ambulatory monitor and a data logging device for measuring and recording penile rigidity and tumescence. The device is linked by cable to a Windows PC, which downloads and processes the data, stores it for review, and prints it on command. The ambulatory monitor-Rigi Scan Plus uses tip and base penile loops that are adjustable by tightening slightly, at discrete time intervals, and allow measuring and recording penile rigidity and tumescence. Each loop contains a cable that moves freely inside a conduit. Each loop takes a measurement every 15 seconds. The loops gently tighten with a linear force of 4 ounces (114 g) and then immediately releases and the tissue rebounds to its unloaded state, thereby taking a tumescence measurement. After the tumescence measurement is taken, it is compared to the previous measurements. When a 6 mm increase in tumescence is detected, representing possible erectile activity, the Rigi Scan Plus Monitor starts taking measurements in 30 seconds intervals. When tumescence is measured, the loops tighten one more time around the circumference of the penis, with a linear force of 10 ounces (283.5 g). The Rigi Scan Plus Monitor takes a measurement when this force is applied, to record a cross-sectional response to radial compression which allows measuring of the rigidity.

Therefore, the Rigi Scan uses two sensors connected to the PC by cables. Due to its complexity, it requires calibration, extensive training of the user as well as interpretation of the results by the physician. Moreover, it requires that the user spends a night in a supervised environment, such as a sleeping room, or a hospital. In addition, due to the application of the two loops and the forces applied, the user may feel discomfort when wearing the device.

Document U.S. Pat. No. 5,782,778 discloses an apparatus and a method for detecting and monitoring the sexual arousal of an individual. The apparatus includes a physiological sensor for sensing the physiological changes of an individual, that correspond to sexual arousal. Generated sensor signals represent the physiological changes. The described apparatus further includes a microprocessor coupled with the sensor for receiving the sensor signals, for converting the sensor signals to control signals, and for storing the control signals. The device further includes a transmitter coupled with and responsive to the microprocessor, for transmitting the stored control signals to a device and for analyzing the control signals in order to monitor the sexual arousal of an individual.

U.S. Pat. No. 4,848,361 A relates to a penile rigidity and tumescence monitoring apparatus comprising transducer means for providing output signals, that indicate penile rigidity and tumescence. The disclosed apparatus further comprises the control means for providing control of the transducer means, for the acquisition and storage of penile rigidity and tumescence data. The transducer means includes readily interchangeable loop-like portions adapted for releasably encircling a penis about the circumference thereof.

Therefore, there is a need for a simple to use, i.e., user-friendly way of automatic tumescence monitoring and recording data indicative of penile tumescence and rigidity. Said data may be further used for obtaining penile health parameters, which can be performed by the user and do not require a physician's presence.

The system according to the present invention operates via wireless i.e. cable-free communication between the components of said system.

The above-mentioned drawbacks of the prior art are solved by the device according to the present invention i.e., by the wearable and non-obstructive device for measuring and monitoring nocturnal penile tumescence in home conditions, without a need to perform the measurement in a supervised environment.

SUMMARY OF THE INVENTION

The device according to the present invention comprises a casing encompassing a reel, the reel having wound up two string threads and a loop formed by two string threads that extend from and are mutually attached outside of the casing. Each string thread is fixed in an outer base channel of the reel by its one end. Further, both threads are partially wound up on said outer base channel of the reel. The opposite end of each of two string threads extends outside of the casing and these two ends of two string threads are connected outside of the device to form a loop to be placed on the base of the penis.

A system for obtaining penis circumference change data comprises a said device, wherein the device is wirelessly connected to a smart device which is further wirelessly connected to a remote computer. The system and the device according to the present invention are used for collecting penile health data and for penile health monitoring.

While the user is asleep, the wearable device continuously monitors changes in penile diameter i.e., the engorgement of the penis. The movement i.e. rotation of the reel, having a spring attached to the reel and a magnet disposed on a disc arranged on the top of the reel, is indicative of a penis diameter. The intensity of erection corresponds to a change in the angular position of a magnet which is detected by a magnetic encoder. Magnetic encoder further converts analog to digital form of data and outputs the digital data to a microprocessor (CPU). The magnetic encoder may be of AS5048A/AS5048B type. CPU calculates the extension of the loop on the basis of the received digital data. The calculated data are forwarded from the CPU to a Bluetooth Low Energy (BLE) communications module, i.e., a communication module that wirelessly transmits the data to a mobile app, installed on a remote BLE enabled-smart device. Optionally, a memory module may be provided on the printed circuit board of the device to store the values directly obtained from the CPU, which are further sent via Bluetooth module to the application installed on the smart device to be stored in the smart device memory. Further, data are downloaded and sent from the mobile app to the cloud, such as a cloud database, to be stored, analyzed, and used for the calculation of various parameters. Further, the analyzed data are sent to the smart device application to be displayed on the smart device in the form of a report. The report may comprise the following data: start and end time of the measurement, total measurement time, date of the measurement, and measurement graph, where the graph is a simple cm/time graph that illustrates the change in the circumference of the penis during the time of the measurement. Furthermore, the report may comprise additional data such as the number of valid erection episodes, total erection time, T score, and additional penile health parameters. T score represents the sum of all the measurements that surpass the erection threshold from the base measurement.

When the user wakes up, the measurement shall be ended on the smart device application, acquired data sent to the remote computer and the device may be removed.

Contrary to the ambulatory monitor disclosed in the prior art, which uses two penile loops, i.e., tip and base penile loops, that adjust by tightening slightly at discrete time intervals to measure and record penile rigidity and tumescence, where the loop gently tightens and then immediately releases and the tissue rebounds to its unloaded state the wearable device according to the present application only needs to be placed on the base of the penis in home conditions, just before going to sleep, in order to obtain the information related to the tumescence. The change of the penile circumference initiates the extension of the loop which causes the rotation of the reel and thereby the change of angular position of the magnet.

Hence, the involvement of a physician is not required. Moreover, there is no need for training the user of the device. The obtained data are analyzed automatically and reported to the user. The data extraction is fully digitalized, with wireless communication between the components of the system.

Furthermore, due to its simplicity and small dimensions realized in a miniaturized, one size fits all manner, a ring-like device is simply placed around the penis by the user himself, just before going to bed. It is non-obstructive and after a few minutes of wearing it, the user hardly feels the presence of the device. Thus, the sleep of the user is not affected.

DETAILED DESCRIPTION OF THE DISCLOSURE

Figure 1:
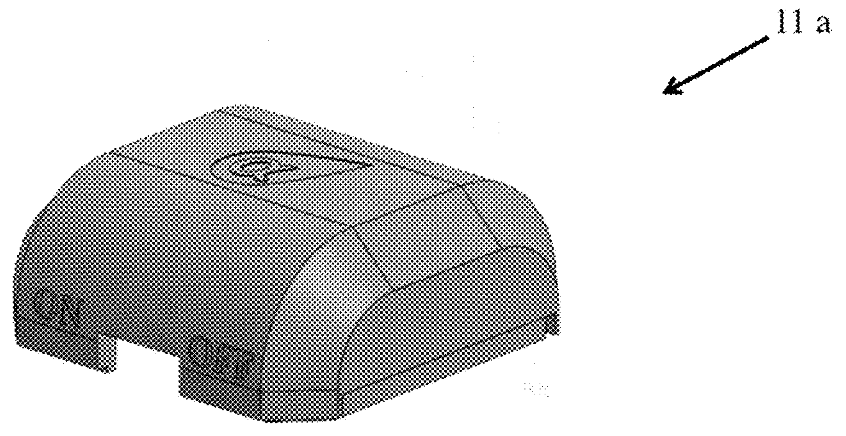
FIG. 1 represents a perspective view of the bottom part of the casing

Device 10 for penile tumescence measurement and monitoring is shown in FIGS. 1 to 9. Device 10 according to the present application is ring-like, and may be worn by the user at the base of the penis, preferably just before going to bed. Device 10 is small in size, compact, and completely non-obstructive, in order to provide comfort while using it. The total dimension of the casing 11, is 32.2×25.5×31.6 mm. The casing material is preferably selected from a biocompatible material having similar properties as the ones being used for dental care. Preferably, the material of the casing may be Nylon PA2200.

Device 10 comprises compact and ergonomic casing 11 having a top part 11*b* and a bottom part 11*a*. The device 10 further comprises a reel 1 within casing 11, having a spring 1*a* positioned in the center of reel 1. One end 25 of spring 1*a* is in connection with the inner side of the top part 11*b* of casing 11. This end 25 of the spring 1*a* is connected to a protrusion 22, preferably a slit 22*a* of a protrusion 22, the protrusion 22 being centrally arranged on the inner side of the top part 11*b* of the casing 11. The opposite end 26 of spring 1*a* passes through the base channel 1*b* of reel 1, and protrudes via reel hole 21 back to the inner side of reel 1, thus stabilizing the spring to reel 1. The device 10 further comprises a magnet 2 centrally attached to disc 14, the disc 14 covering the top side 1*c* of the reel. The device 10 according to the present invention further comprises a printed circuit board 4 (PCB) having a magnetic rotary encoder 5 disposed on the PCB, a microprocessor 6 (CPU), and a communication module 7, such as Bluetooth Low Energy communications module (BLE). Furthermore, device 10 comprises loop 3, formed by two string threads 23 and 24. Both string threads 23, 24, by one end thereof, are fixed at the fixing point 20 of the reel 1 and both threads are partially wound on the outer base channel 1*b* of the reel 1. The opposite end of each of the string threads extends outside of the top part 11*b* of the casing 11 and these two ends are mutually attached outside of the device 10 to form a loop 3.

The bottom part 11*a* of casing 11 comprises the printed circuit board (PCB) 4. PCB may be differently shaped, for example, may be ellipsoidal, square, or round-shaped. PCB is preferably round-shaped, with a 2.5 cm diameter, and has double-sided component placement, i.e., bottom side 4*b* and top side 4*a* component placement on the PCB. The magnetic rotary encoder 5 is positioned at the top side 4*a* of the printed circuit board 4 adjacent to and facing magnet 2 when both parts (11*a*, 11*b*) of casing 11 are assembled together. The magnetic rotary encoder 5 is a special integrated circuit (I.C.) arranged to measure the position of the rotation angle of the magnet 2 i.e., the angular position of the magnet 2. Furthermore, the I.C. contains integrated Hall sensors and is placed at the center of the PCB. The I.C. is programmed with algorithms, the algorithms being Analog-to-Digital Converter (ADC) and Digital Signal-Processing (DSP) algorithms. Based on these algorithms the I. C. is arranged to provide an accurate high-resolution absolute angular position information in a digital format to a microprocessor 6 (CPU) placed on the bottom side 4*b* of the printed circuit board 4. The microprocessor 6 and the communication module 7, such as the Bluetooth Low Energy communications module, are arranged at the bottom side 4*b* of the printed circuit board 4. Additionally, device 10 has a power supply unit 8 that may include a battery 8*a* and a micro-USB port 8*b*. Device 10 further includes an on/off switch 12.

Figure 3:
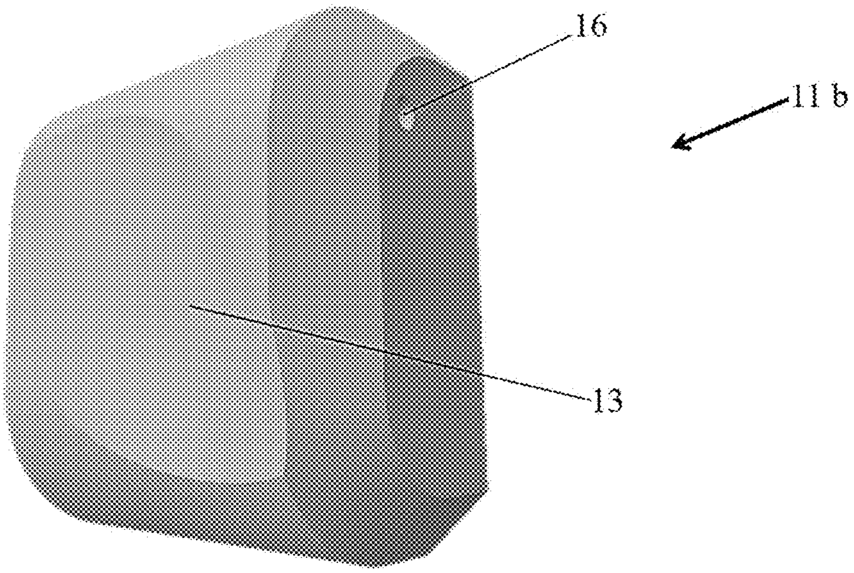
FIG. 3 represents the outer view of the top part of the casing showing indentation
Figure 4:
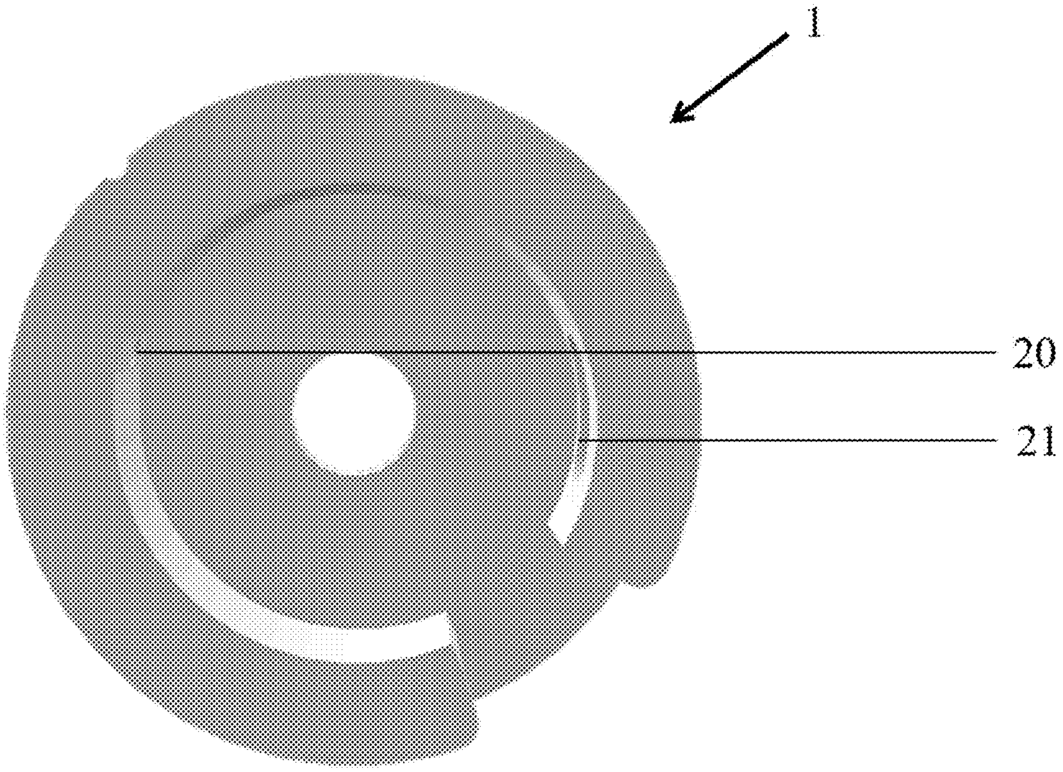
FIG. 4 represents the top view of the reel
Figure 5:
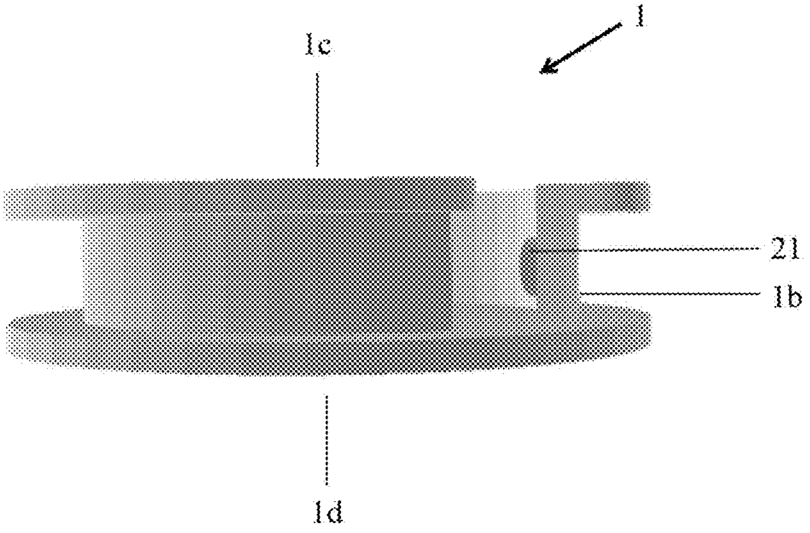
FIG. 5 represents a side view of the reel
Figure 6:
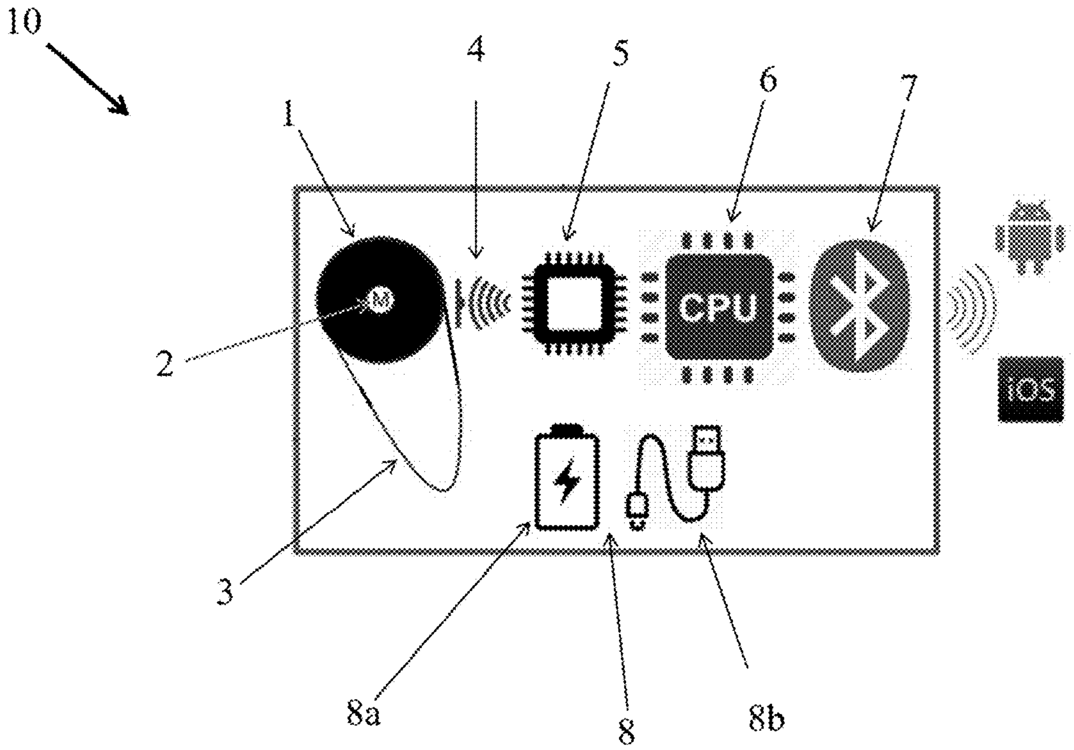
FIG. 6 represents a block diagram of the monitoring system
Figure 7:
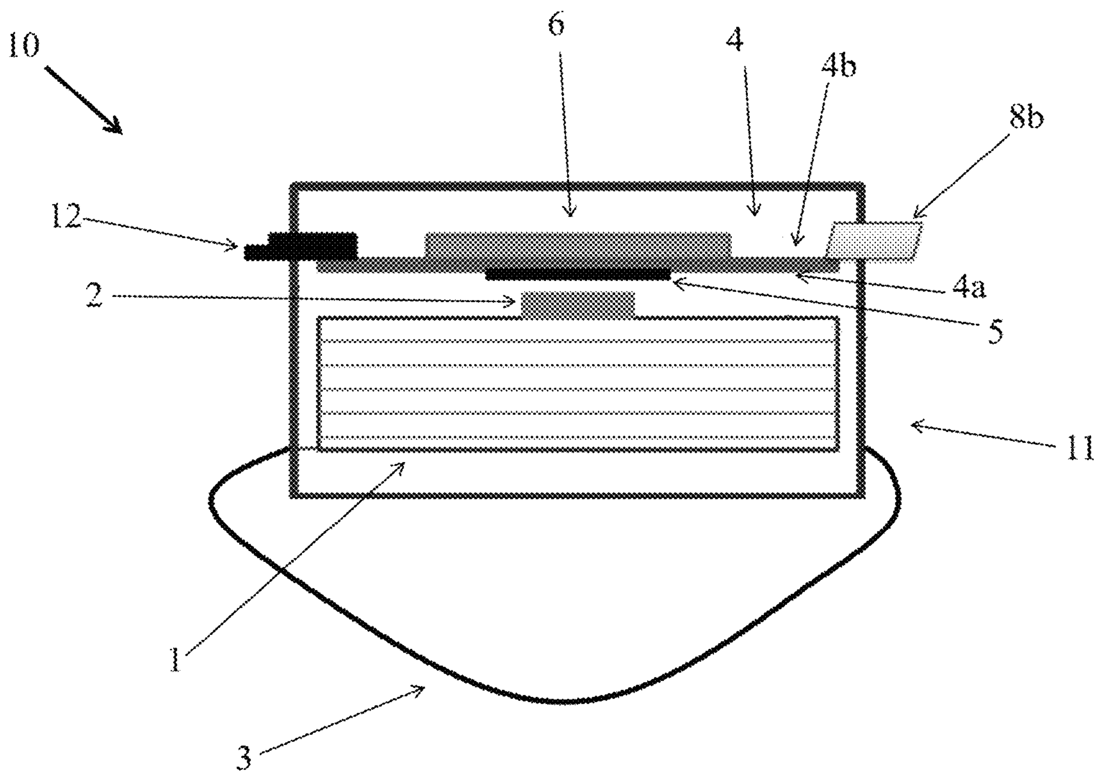
FIG. 7 represents the block diagram, i.e. the cross-sectional view of the wearable device.
Figure 8:
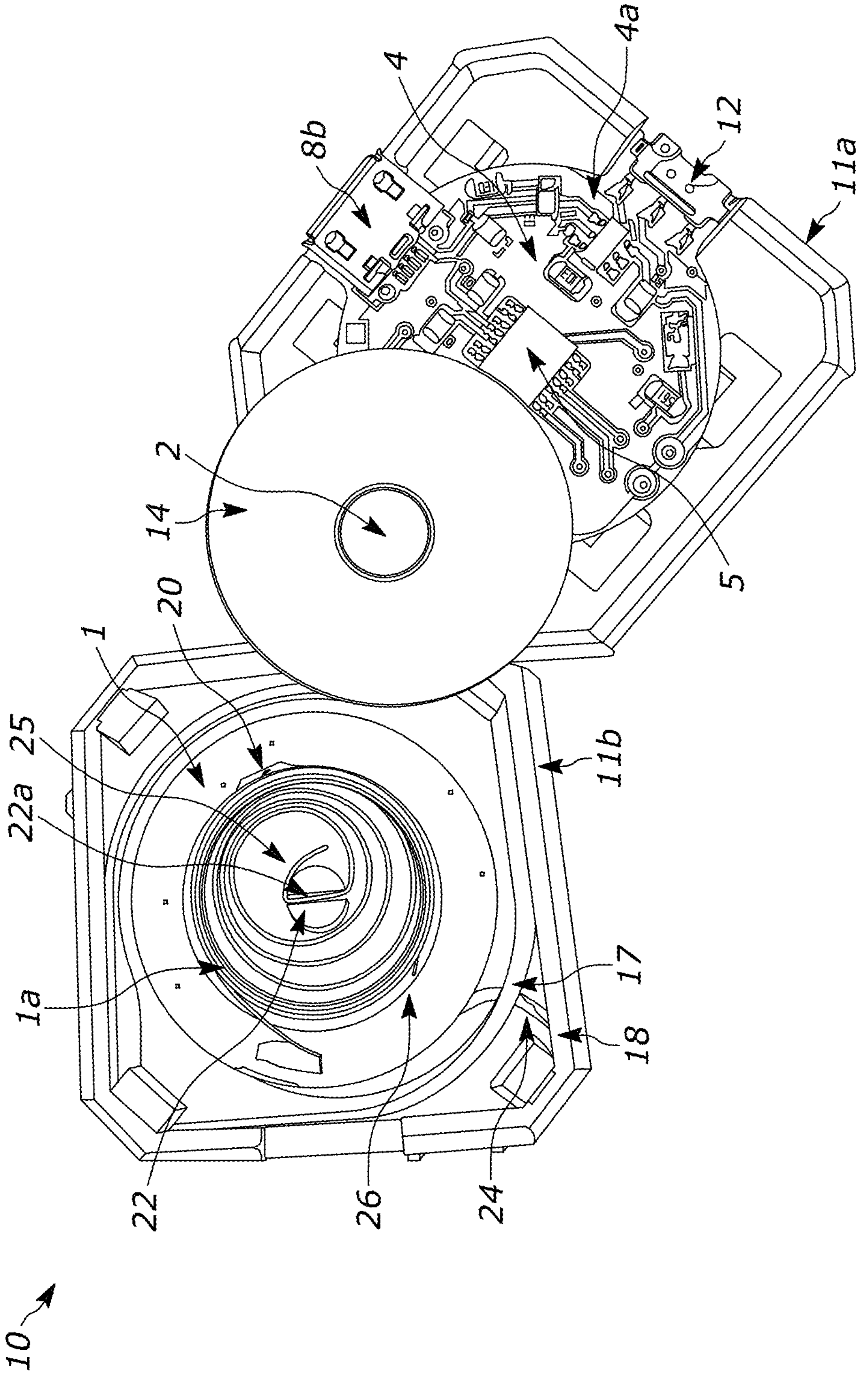
FIG. 8 represents the inner view of the top and bottom parts of the casing of the device.
Figure 9:
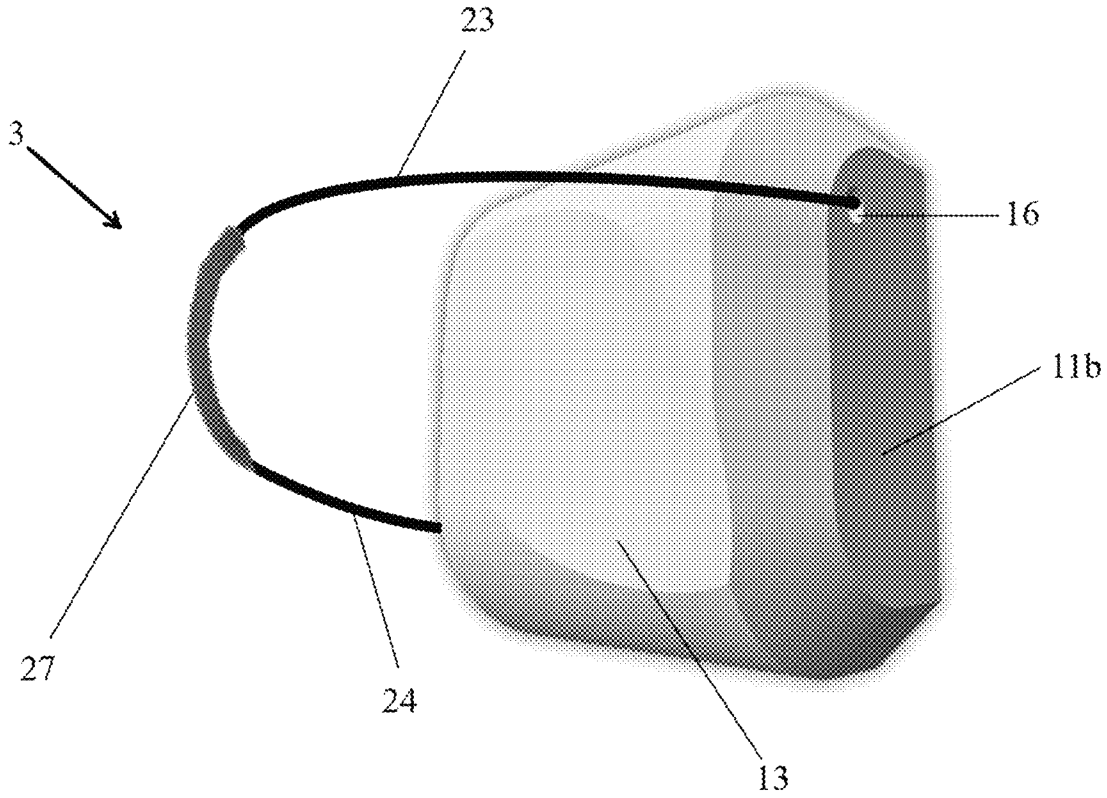
FIG. 9 represents the outer view of the top part of the casing showing indentation and an extended loop of the string threads with the covering strap covering the attachment point.
Figure 10:
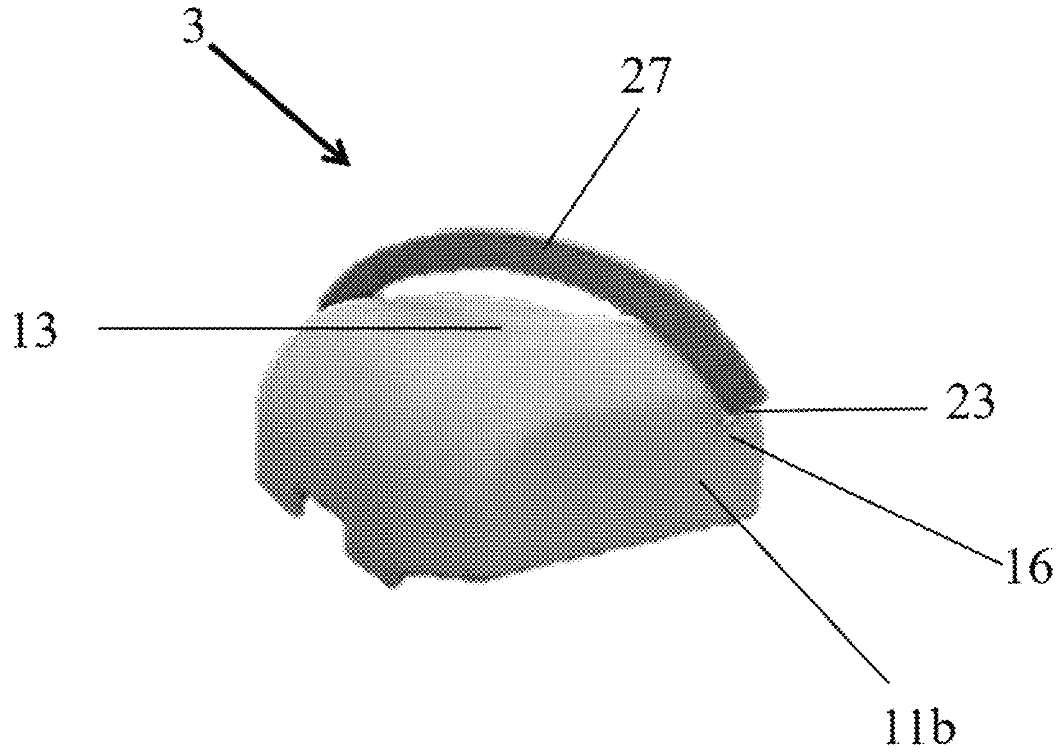
FIG. 10 represents the outer view of the top part of the casing showing indentation and a loop of the string threads with a covering strap covering the attachment point.

The top part 11*b* of the casing 11 has an indentation 13 in the middle of the outer surface i.e., the surface which is in contact with the penis (see FIG. 3 and FIG. 9). Said indentation 13 ensures comfortable use by the user when the device 10 is in contact with the user's penis. The top part 11*b* of casing 11, as previously disclosed, houses reel 1, rotatably attached to protrusion 22 of casing 11.

Figure 2:
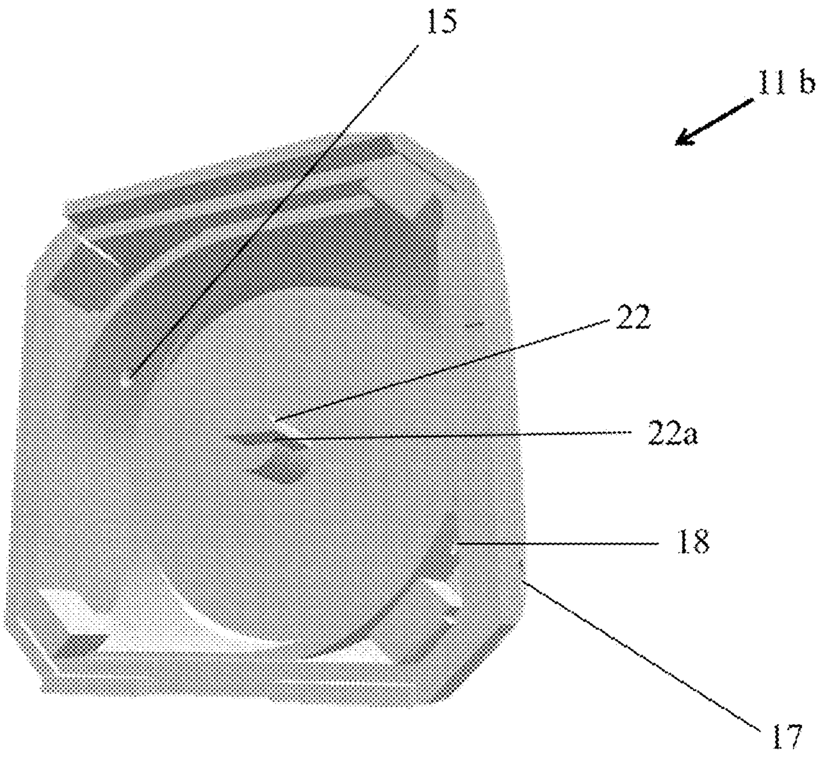
FIG. 2 represents the inner view of the top part of the casing

The top part 11*b* of the casing 11 is further provided with holes 15, 17, 18 (FIG. 2) and 16 (FIG. 3). The holes 15, 16, 17, 18 are arranged to provide the passage for the string threads 23 and 24 coming out from the casing 11 and being attached outside of the casing 11 to form the loop 3. The holes 15 and 16, are positioned on one side of the top part 11*b* of the casing 11, providing passage for the string thread 23 while the holes 17 and 18 are located on the opposite side of the top part 11*b* of the casing 11, providing passage for the string thread 24 (FIG. 2).

Each of the two string threads is fixed in the outer base channel 1*b* of reel 1 at the fixing point 20. Both threads are at least partially wound on said outer base channel 1*b* of reel 1. One string thread 23 passes through the holes 15 and 16, while the other string thread 24 passes through the holes 17 and 18 and both string threads reach the outside of the top part 11*b* of the casing 11. String threads are attached by their ends and at least partially covered by a covering strap 27, preferably a silicon tube, outside of the casing 11 to form a loop 3, which shall be placed around the penis.

The string threads 23 and 24, and consequently the loop 3, may be differently shaped. The string threads 23 and 24, and consequently the loop 3 are preferably tube-shaped and made of soft material, preferably silicon.

Both threads 23, 24 are attached to one another at the fixing point 20, for example by being tied in a knot. Further, the opposite ends of each string thread 23, 24 are partially wound around reel 1 and subsequently extended to the outside of the top part 11*b*.

The reel hole 21 on reel 1 (FIG. 4) may be differently shaped. The reel hole 21, preferably ellipsoidal in shape, stabilizes spring 1*a*, i.e., the opposite end 26 of spring 1*a*, which is opposite to the end 25 of spring 1*a*. The term stabilizing means that said opposite end 26 of spring 1*a* rotates together with reel 1 (it is pulled by the reel), thus having no degree of freedom to move without the movement of reel 1.

Reel 1 of device 10 has two sides: top side 1*c* and bottom side 1*d*. The top side 1*c* of the 1 faces the top side 4*a* of the printed circuit board 4. The top side 1*c* of reel 1 has a disk 14 attached to it, with centrally positioned magnet 2 on disc 14, facing the magnetic rotary encoder 5. The size of the magnet is preferably between 6 and 8 mm in diameter, and the height of the magnet is preferably ≥2.5 mm, the height being measured from the base of the magnet 2.

FIG. 9 represents the top part 11*b* of casing 11 showing indentation 13 and loop 3 of the string threads 23 and 24. In this figure, the covering strap 27 is also shown. The covering strap 27, covers the attachment of the string threads 23 and 24, i.e., the point where both strings are attached, in order to form the loop 3. The covering strap 27 is of a protective soft material that protects the soft outer tissue of the penis from an injury, which can be caused by the attachment point of the two string threads 23 and 24. The covering strap 27, preferably covers at least the attachment point of the two string threads 23 and 24, i.e. only partially covers the loop 3.

The operation of device 10 is described as follows. In order to provide the tumescence monitoring, loop 3 formed by the two string threads 23, 24, which extend from the casing 11, shall be placed around the penis encompassing the base of the penis. At the occurrence of night erections, the penis changes its diameter, which leads to the extension or shortening of the loop 3, formed by the two string threads 23, 24, which extend out from the casing 11. Inside of casing 11, these two string threads 23, 24 are partially wound up on the outer base channel 1*b* of reel 1.

During the engorgement of the penis, loop 3 extends, i.e. the two string threads 23, 24 extend outside the casing 11, causing the reel 1 to rotate. The string threads 23, 24 are wound on the reel 1 in the same direction. During the extension of loop 3, string threads 23, 24 are unwinding from the outer base channel 1*b*, and reel 1 rotates in one direction, while during the retraction of loop 3, string threads 23, 24 are winding on the outer base channel 1*b* and the reel 1 rotates in opposite direction.

The rotation of reel 1 at the same time causes rotation of the disk 14 and thus the rotation of magnet 2. As stated before, magnet 2 is attached and centrally positioned on disk 14, said disk being further attached on the top side 1*c* of the 1. The alternating magnetic field is monitored by the magnetic rotary encoder 5 which is placed at the top side 4*a* of the printed circuit board 4 adjacent to and facing the magnet 2. The magnetic rotary encoder 5 outputs the corresponding alternating magnetic field data to the microprocessor 6 placed on the bottom side 4*b* of the printed circuit board 4. Said data are indicative of the time and value of the loop extension. The received data are then processed by microprocessor 6, and the extension of loop 3 is calculated using algorithms implemented in the microprocessor 6 firmware, i.e. based on the degree of rotation of the magnet 2 and the diameter of the outer base channel 1*b*. Thus, device 10 provides information reflecting the circumference change of the penis every second in real time.

In order to start the monitoring of the circumference change of the penis, the user shall extend loop 3, and place the casing 11 on the base of the penis with loop 3, embracing the penile base. Loop 3 encircles the penis, and in cooperation with spring-loaded reel 1 holds device 10 in place.

Optionally, the device may be accompanied by a cover, in order to further protect the penis and hold the device 10 in one position.

The data collected by device 10 reflect the values of the diameter of the penis when in a flaccid state and when in an erect state, whereby said values of the diameter correspond further to erection intensity during the erection episodes. In one aspect, the communication module 7 is in constant communication with the smart device in order to transmit the data processed by the microprocessor 6. Namely, the data is transmitted each second via communication module 7, such as Bluetooth Low Energy communications module, to a user's smart device, i.e., smartphone. The smart device contains the application which acquires the data from the device 10. The acquired data are stored locally in the memory of the smart device.

Upon completion of monitoring of the circumference change of the penis, the application installed on the smart device uploads all the recorded data to the remote computer such as a cloud database, where the data are analyzed by an algorithm. The remote computer may store, calculate and analyze various parameters and generate various reports to be provided to the user.

In another aspect, the acquired data are stored locally by the memory module provided in the PCB of device 10.

Upon completion of monitoring of the circumference change of the penis, the recorded data are uploaded to a cloud database, preferably to a remote computer, where the data are analyzed by an algorithm. The remote computer may store, calculate and analyze various parameters and generate various reports to be provided to the user.

Device 10 according to the present invention may be applied for obtaining data on the circumference change of the penis. The method for application of the device 10 and the system comprises the following steps:

- positioning the device 10 according to the present invention on the base of the penis;
- detection and measurement of the change of angular position of magnet 2 by the magnetic encoder 5;
- generating digital format of the measurement data by the magnetic encoder 5;
- communicating the digital format of the measurement data from the magnetic encoder 5 to the microprocessor 6;
- processing the data received by the microprocessor 6 by calculating the extension of the loop based on the degree of the rotation of magnet 2 and the diameter of the outer base channel 1*b;*
- wirelessly transmitting the processed data from the microprocessor 6 to the memory module provided on the PCB of device 10 or to the smart device;
- storing the processed data;
- uploading the stored data to a cloud, such as a cloud database for storing, analyzing, and using for the calculation of various parameters;
- generating the report;
- transmitting the generated report to the smart device and displaying the report on the smart device.

The device 10 shall be placed on the base of the penis, turned on, and connected over BLE to the smart device. The magnetic encoder 5 shall measure the change of angular position of magnet 2 and generate the digital format of the measured data. The digital data shall be communicated from the magnetic encoder 5 to a microprocessor 6, and data received by the microprocessor 6 shall be processed and the extension of the loop calculated based on the degree of the rotation of the magnet 2 and the diameter of the outer base channel 1*b*. The data may be further stored directly from the CPU in the memory module provided on the PCB. The calculated data shall be wirelessly transmitted from the microprocessor 6 to the smart device, such as a smartphone, and the acquired data stored in the smart device's memory. Such stored data shall be transmitted to the remote computer for storing, analyzing, and using for the calculation of various parameters. The various parameters shall be transmitted from the remote computer to the smart device and represented in the form of the report sent to the user.

Preferably, 1 sample per second is acquired, i.e. so during 8h of sleep, 28800 samples may be acquired. Preferably, the first 5 mins (300 samples) of the measurement of the change of angular position of the magnet 2 by the magnetic encoder 5 is discarded, to avoid loop extension adjustment errors created by the user during the positioning of the device.

The minimum and maximum tumescence levels measured are used for the determination of an erection threshold.

A valid erection episode is detected if the value of the change of angular position of the magnet 2 is above the erection threshold and lasts during a particular period of time, which is the first period of time, i.e. valid erection episode. Particularly, if during the first period of time, which may last for example for 5 min, the value of the change of angular position of magnet 2 falls below the erection threshold once or more than once, depending on the length of the first erection time, and where such value lasts for a predetermined period of time i.e. second period of time, for example for 1 min during the 5 min long first period of time, the second period of time will be omitted from the data analyses. Otherwise, if during the first period of time, the value of the change of angular position of magnet 2 falls below the erection threshold for longer than the predetermined period of time, for example for longer than 1 min, preferably 2-3 min, then the second period of time shall not be omitted from the data analyses and shall be accounted as an end of the first erection episode.

During an overnight sleep, most healthy men will experience 3-5 erections episodes. It is important to keep the erection mechanism healthy in order to provide highly oxygenated blood to the erectile tissue. Conversely, impaired night erections reduce tissue oxygenation and increase penile fibrosis (formation of scar tissue in the penis) which leads to further worsening of night erections. This may result in progressive erectile dysfunction (ED).

Device 10 according to the present application enables tracking of the additional markers for erection health, i.e. the total duration of all recorded erection episodes. Most men will have a total erection time of at least 45 min after an overnight sleep i.e., during 7-8 hours. The total duration of the erection correlates with the penile condition. Thus, device 10 enables monitoring the total erection time during an overnight sleep.

The score is used to evaluate the overall quality of night erections during the measurement. Every man will have a different initial score, so there is no normal range. However, an increase in the total erection time will indicate that night erections are improving. The total erection time is measured as a sum of all the measurements that surpass the erection threshold.

Thus, the present application discloses a monitoring system comprising the device wirelessly connected to a smart device, wherein the smart device is wirelessly connected to a remote computer. The smart device is configured to receive the data from the device over the BLE and to perform recording, storing, and transmitting the measurement data to the remote computer and further displaying the report obtained from the remote computer. The remote computer is configured to store and analyze the received data and to calculate the penile health parameters.

Using the parameters to measure and track the night erections, it can be determined whether the user has erectile dysfunction or erectile dysfunction-like symptoms or a psychological issue.

REFERENCE SIGNS

1 Reel
1*a* Spring
1*b* Outer base channel
1*c* The top side of the reel
1*d* Bottom side of the reel
2 Magnet
3 Loop
4 PCB (Printed circuit board)
4*a* Top side of the PCB
4*b* Bottom side of the PCB
5 Magnetic rotary encoder
6 Microprocessor (CPU)
7 Communication module (Bluetooth Low Energy communications module (BLE))
8 Power supply unit
8*a* Battery
8*b* Micro USB charge port
10 Device
11 Casing
11*a* Bottom part of the casing 11
11*b* Top part of the casing 11
12 On/off switch
13 Indentation

14 A disk having the magnet
15,16 Holes on one side of the top part of the casing
17,18 Holes on the opposite side of the top part of the casing
20 Fixing point
21 Reel hole
22 Protrusion
22: Slit
23.24 String threads
25.26 Ends of the spring
27 Covering strap

The invention claimed is:

1. A device (10) for obtaining penis circumference change data during penile tumescence monitoring comprising:
   - a casing (11) comprising a top part (11*b*) and a bottom part (11*a*), the casing further comprising holes (15, 16, 17, 18) and a reel (1) which is arranged within the casing (11) and rotatably connected to the casing (11),
   - a spring (1*a*) arranged in the reel (1) and operably connected to the reel (1) by one end (26) thereof and to the casing (11) by an opposite end (25) thereof,
   - a magnet (2) centrally positioned on a disc (14), the disc (14) covering the reel (1),
   - a printed circuit board 4 (PCB) arranged in the casing (11) comprising a magnetic rotary encoder (5) and a microprocessor (6), the magnetic rotary encoder (5) operably arranged to measure the position of the rotation angle of the magnet (2) and to output the measured data to the microprocessor (6) for processing the received data, the magnetic rotary encoder (5) being adjacent to and facing the magnet (2), said PCB (4) further comprising a communication module (7) arranged to transmit data,
   - a loop (3), formed by two string threads (23, 24),
   - wherein the microprocessor (6) are configured to determine an extension of the loop (3), and thereby the penis circumference change data, based on a degree of rotation of the magnet (2) measured by the magnetic rotary encoder (5) and a diameter of the outer base channel (1*b*) of the reel (1);
   - wherein the two string threads (23, 24) are mutually attached within the reel (1) at a single common fixing point (20) by one end of each string thread, and both string threads (23, 24) entering into a commonan outer base channel (1*b*) of the reel (1), are partially wound up on said outer base channel (1*b*) of the reel (1), while the opposite ends of the string threads (23, 24) extend outside of the casing (11) through the respective holes (15, 16, 17, 18) with a first one of the string threads (23) extending through first holes (15, 16) positioned on one side of the top part (11*b*) of the casing (11) and a second one of the string threads (24) extending through second holes (17, 18) positioned on an opposite side of the top part (11*b*) of the casing (11), and said threads (23, 24) are mutually attached outside of the device (10) forming the loop (3).

2. The device (10) according to claim 1, wherein the PCB (4) further comprises a memory module configured to store the data received from the microprocessor (6).

3. The device (10) according to claim 1, wherein the casing (11) comprises a top part (11*b*) having a protrusion (22) and a bottom part (11*a*).

4. The device (10) according to claim 3, wherein the spring (la) is connected by one end (25) thereof to the protrusion (22) centrally arranged on the inner side of the top part (11*b*) of the casing (11) and the opposite end (26) of the spring (1*a*) passes through the base channel (1*b*) of the reel (1), and protrudes via a reel hole (21) back to the inner side of the reel (1).

5. The device (10) according to claim 3, wherein the protrusion (22) comprises a slit (22*a*) connected with the end (25) of the spring (la).

6. The device (10) according to claim 1, wherein the magnetic rotary encoder (5) is programmed with algorithms, said algorithms being Analog-to-Digital Converter (ADC) and Digital Signal-Processing (DSP) algorithms.

7. The device (10) according to claim 1, wherein the magnetic rotary encoder (5) contains integrated Hall sensors.

8. The device (10) according to claim 1, wherein said device (10) comprises a power supply unit (8), the power supply unit (80) including a battery (8*a*) and a micro-USB port (8*b*).

9. The device (10) according to claim 1, wherein the holes (15, 16, 17, 18) are arranged at the top part (11*b*) of the casing (11) the holes (15,16) being positioned on one side of the top part (11*b*) of the casing (11), providing passage for the string thread (23) and the holes (17, 18) being positioned on the opposite side of the top part (11*b*) of the casing (11), providing passage for the string thread (24).

10. The device (10) according to claim 1, wherein the magnet (5) is preferably between 6 and 8 mm in diameter, and the height of the magnet is ≥2.5 mm, the height being measured from the base of the magnet (2).

11. A system for obtaining penis circumference change data, the system comprising the device (10) according to claim 1, wherein the device (10) is wirelessly connected to a cloud database for recording, storing, and analyzing the received data.

12. The system according to claim 11, wherein the device (10) is wirelessly connected to a smart device for storing the data, which is wirelessly connected to the cloud database for recording, storing, and analyzing the received data.

13. A method of application of the device (10) according to claim 1, the method comprising the following steps:
   - positioning the device (10) on the base of the penis;
   - registering and measurement of the change of angular position of the magnet (2) by the magnetic encoder (5);
   - generating digital format of the measurement data by the magnetic encoder (5);
   - communicating the data from the magnetic encoder (5) to the microprocessor 6);
   - processing the digital data by the microprocessor (6) by calculating the extension of the loop based on the degree of the rotation of the magnet (2) and the diameter of the outer base channel (1*b*);
   - wirelessly transmitting the processed data from the microprocessor 6 to the memory module provided on the PCB of device 10 or to a smart device;
   - storing the processed data;
   - uploading the stored data to a cloud, such as a cloud database for storing and analyzing the data;
   - receiving a generated report on the smart device and displaying the report on the smart device.

* * * * *